United States Patent [19]

Shikhashvili et al.

[11] Patent Number: 5,997,876
[45] Date of Patent: Dec. 7, 1999

[54] BURN AND WOUND OINTMENT

[76] Inventors: Nino Shikhashvili, Building 5, Apt. 77, Mukhiani Settlement 3, Tbilisi, Ga. 38072; Zurab Darsavelidze, Building 13, Apt. 61, Gldani Settlement 8, Tbilisi, Ga. 38012

[21] Appl. No.: 09/180,635
[22] PCT Filed: May 8, 1997
[86] PCT No.: PCT/GE97/00001
  § 371 Date: Nov. 10, 1998
  § 102(e) Date: Nov. 10, 1998
[87] PCT Pub. No.: WO97/42963
  PCT Pub. Date: Nov. 20, 1997

[30] Foreign Application Priority Data

May 10, 1996 [GA] Gabon ........................ 002274

[51] Int. Cl.$^6$ .............................. A61K 35/78; A61K 9/06
[52] U.S. Cl. .............. 424/195.1; 424/443; 424/DIG. 13; 514/886; 514/969
[58] Field of Search ................ 424/195.1, 443, 424/DIG. 13; 514/969, 886

[56] References Cited

U.S. PATENT DOCUMENTS 4,459,285  7/1984  Grollier et al. ............................ 424/74
5,061,491  10/1991  Deryabin ................................ 424/195.1

FOREIGN PATENT DOCUMENTS

671336 A5  8/1989  Switzerland .

OTHER PUBLICATIONS

Database Derwent Publications, No. 97–049981, Leontev et al. 'Balsam composition with wound–healing properties comprising camphor, essential oil concentrate containing oil from mint and one other plant, and herb mixture edible oil extract,' abstract, Make, Jan. 1995.

Database Derwent Publications, No. 95–342794, Purakhina et al. Anitbacterial cream for persona saintary use contains dry extracts of St. John's Wort and bur marigold, yarrow grass and calendula flowers, liquorice root, sea buckthorn berries, and ointment, Mar. 1995.

Database Derwent Publications, No. 96–107601, 'Preparation of dermatology cream type cerate comprises thermostated agitated blending of plant fractions, e.g. *Chelidonium majus* and *Plantago lanceolata*,' Soria Natural SA, Jan. 1996.

*Primary Examiner*—Thurman K. Page
*Assistant Examiner*—Alysia Berman
*Attorney, Agent, or Firm*—Abelman, Frayne & Schwab

[57] ABSTRACT

This invention refers to the sphere of medicine, in particular to pharmaceutics and concerns the preparations for burn treatment. The technical result of the present invention is in widening the assortment of medicinal preparations for treatment of bums and wounds, in increasing treatment effect. The ointment contains the components in the following relation of mass parts:

| celandine | *Chelidonium majus* | 15–25 g |
| plantain | *Plantago major* | 15–25 g |
| matricary | *Matricaria chamomilla* | 15–25 g |
| yarrow | *Achillea millefolium* | 15–25 g |
| calendula | *Calendula officinalis* | 15–25 g |
| St. John's-wort | *Hypericum perforatum* | 15–25 g |
| gum-tree | *Eucalyptus globulus* | 15–25 g |
| olive oil | *Oleum olivarum* | 1000 g |
| yellow wax of honey | *Cera flava* | 80–130 g |

2 Claims, No Drawings

BURN AND WOUND OINTMENT

This application is a 371 of PCT/GE97/00001 filed May 8, 1997.

This invention refers to the sphere of medicine, in particular to pharmaceutics and concerns the preparations for bum treatment.

There is known calendula ointment Unguentum "Calendula", which contains tincture of calendula (on 70% spirit 1:10)—20 g, vaseline—90 g: [Mashkovskij M. V. "Medicinal Means", Moscow, "Medicine" 1986, vol. 2, p. 2.424].

At using this ointment on wound and burn the process of healing is slowed down, as the ointment contains only one medicinal preparation and vaseline. vaseliine makes crust on the injured surface, under which the microbes are easily reproduced.

There is also known "Ointment Kolkhuri", which contains St.John's-wort. the oak bark, haw-thom, yarrow, yellow melilot, horse-chestnut 0.06–0.065 in equal quanity, nettle 0.10–0.11, gum-tree extract 0.02, belladonna extract 0.02, vaseline—the rest; [GE 13, Darsania, V. 15.05.94].

This ointment is used as analgetic and antiinflammatory means and is less effective for healing the wounds and burns, as haw-thorn and belladonna arc not characterized by antiinflammatory and regeneration stimulating effect. The yellow melilot and horse-chestnut contain substances which hinder the blood coagulation and do not effect the skin regeneration. The oak bark and nettle have antiinflammatory properties, but it must be mentioned, that tannin involved in oak bark in reaction with the injured surface mucous membrane proteins at burn makes a coat, under which purulent process occurs. The nettle increases the quantity of erythrocytes and hemoglobin, which is raised at burn in result of intensified loss of plasma.

The technical result of the present invention is in widening the assortment of medicinal preparations for treatment of burns and wounds, in increasing treatment effect.

The technical result is achieved by that the green ointment, which contains St.John's-wort, yarrow, gum-tree, additionally contains celandine, plantain, matricary, calendula, olive oil and yellow wax of honey in the following relation of components in mass parts:

| | | |
|---|---|---|
| celandine | Chelidonium majus | 15–25 g |
| plantain | Plantago major | 15–25 g |
| matricary | Matricaria chamomilla | 15–25 g |
| yarrow | Achillea millefolium | 15–25 g |
| calendula | Calendula officinalis | 15–25 g |
| St. John's-wort | Hypericum perforatum | 15–25 g |
| gum-tree | Eucalyptus globulus | 15–25 g |
| olive oil | Oleum olivarum | 1000 g |
| yellow wax of honey | Cera flava | 80–130 g |

The additional application of celandine, plantain, matricary, calendula, olive oil and yellow wax of honey in the ointment in the said relation of components in mass parts enables to increase treatment effect, which is provided by the properties of the grass.

Celaudine—is characterized by antiinflammatory, local analgetic, regeneration accelerating effect.

Plantain—is characterized by antimicrobic, hemostasia and wound healing effect.

Matricary—is characterized by antiseptic, local analgetic and antiinflammatory effect, accelerates regeneration.

Calendula—strengthens the circulatory vessels walls, reduces their permeability, what is very important at burn, when the capillary conduction and plasinorrhea is increased. Calendula's effect grows in combination with matricary and yarrow, skin epitalization and granulation, local protective mechanisms increase.

Olive oil—has deeper effect than the vaseline, the skin absorbs it easily.

Honey wax—contains large quantity of vitamin A, which is necessary, for recovery of skin entirety and provides for fast healing of the burn.

Besides, the increase of the quantify of celandine, plantain, matricary, calendula. yarrow, St.John's-wort, gum-tree in green ointment more than 25 g, of the olive oil more than 1000 g and of the honey yellow wax more than 130 g doesn't promote the treatment efficiency and results in over-expenditure of the raw.

At the same time the reduction of the quantity of celandine, plantain, matricary, calendula, yarrow, St.John's-wort, gum-tree below 15 g, of the olive oil below 1000 g and of the honey yellow wax below 80 g increases the time of treatment and reduces its efficiency.

Method for preparing of green ointment is carried out in the following way:

small grinded grass—15–25 g of celandine, 15–25 g of plantain, 15–25 g of matricary, 15–25 g of calendula, 15–25 g of yarrow, 15–25 g of St.John's-wort, 15–25 g of gum-tree is filled in enamel vessel, 1000 g of olive oil is poured in and boiled on water bath during 6 hours, cooled to room temperature and pressed out.

The obtained oil mass of 700–900 g is boiled again on water bath and mixed with small cut honey wax Of 80–130 g. boiled for 30 minutes, put away and stirred until cooling to room temperature.

EXAMPLE 1

Small grinded dried grass—15 g of calendine, 15 g of plantain, 15 g of matricary, 15 g of calendula, 15 g of yarrow, 15 g of St.John's wort, 15 g of gum-tree is filled in enamel vessel, 1000 g of olive oil is poured in and boiled on water bath during 6 hours, cooled to room temperature and pressed out. The obtained oil mass of 900 g is boiled again on water bath and mixed with small cut 105 g honey wax, boiled for 30 minutes, put away and stirred until cooling to room temperature.

EXAMPLE 2

Small grinded dried grass—20 g of calendine, 20 g of plantain, 20 g of matricary, 20 g of calendula, 20 g of yarrow, 20 g of St.John's wort, 20 g of gum-tree is filled in enamel vessel, 1000 g of olive oil is poured in and boiled on water bath during 6 hours, cooled to room temperature and pressed out. The obtained oil mass of 800 g is boiled again on water bath and mixed with small cut 105 g honey wax, boiled for 30 minutes, put away and stirred until cooling to room temperature.

EXAMPLE 3

Small grinded dried grass—25 g of calendine, 25 g of plantain, 25 g of matricary, 25 g of calendula, 25 g of yarrow, 25 g of St.John's-wort, 25 g of gum-tree is filled in enamel vessel, 1000 g of olive oil is poured in and boiled on water bath during 6 hours, cooled to room temperature and pressed out. The obtained oil mass of 700 g is boiled again on water bath and mixed with small cut 130 g honey wax, boiled for 30 minutes, put away and stirred until cooling to room temperature.

According to said examples the ointment was applied on the members of the inventor's family and volunteers at treatment of I, II, III degree burns, of lacerated, contused, incised wounds. At applying the bandage, with patients there was marked—arrest of bleeding, reduction of pain, stoppage of purulent discharge, acceleration of granulation and epithelization. There were not cases of treatment complication, such as suppuration, bleeding, occurrence of the thick coat on the surface, prolongation of wound healing. The ointment effect was marked at the burn of III degree, when all the sources for epithelium reproduction in the injured area needed for skin regeneration are destroyed.

1. Patient E.D.—woman, 36 years old, resident of Tbilisi, Marjanishvili str. 46.

Diagnosis: burn of III degree.

There was burned more than 50% of body surface, after treatment in the hospital during 3 months flection surface of the right hand from armpit to hand and chest was left unhealed. The only way for healing the wound was skin transplantation, which the patient categorically refused and decided to begin treatment with green ointment. Objectively the muscle layer was injured on different depth, there was marked bleeding, violent pain, swelling of the tissues around. In several minutes after applying the ointment the patient felt easing of tension, pain, arrest of bleeding. The ointment was applied every day during a month, gradually in the injured area skin tubercles occurred, the granulation tissue grew intensively without suppuration and coating. The wound was healed in a month without scars.

2. Patient Sh.N.—woman, 44 years old, resident of Tbilisi.

Diagnosis: burn of II degree. The hand was injured, was marked violent redness with different quantity of vesicles with serous exudates. The ointment was applied 2 times a day during 10 days. The injury healed without suppuration.

3. Patient T.B. child, 3 years old, resident of Tbilisi.

Diagnosis: lacerated wound.

The child's hand was lacerated with obtuse subject, the wound was not sutured, in three days after applying the ointment the wound was filled without scars.

4. Patient Z.N.—woman, 71 years old. resident of Tbilisi.

Diagnosis: burn of II degree.

With the patient there was marked redness of lower extremities, vesicles of different sizes filled with liquid. The ointment was applied every day during 3 weeks. The injury healed without scars.

5. Patient I.I.—man, 57 years old, resident of Tbilisi.

Diagnosis: lacerated wound.

The patient's hand was lacerated deeply with an obtuse subject. The wound was not sutured. the ointment was applied every day during one week. The wound healed without scars.

The pre-clinical investigations of the new medicinal means green ointment were carried out in the Institute for Experimental and Clinical Medicine of Tbilisi State University by GLP Program "The rules of Pre-Clinical Estimation of Pharmacological Means", RD 64-126-91, Moscow 1992.

The mechanism of action of the green ointment on the body was studied by toxicological, microbiological, morphological, immunological, pathophysiological, histostructural, biochemical methods.

Green ointment is non-toxic. Its $LD_{50}$ is more than 320-fold therapeutic dose, which is equal to 9152.0 mg/kg. green ointment is not characterized by cumulative properties. Cumulation $LD_{50}$ is more than 960-fold therapeutic dose, which is equal to 27456.0 mg/kg. The ointment is not characterized by allergic or local-irritation action.

The results of the investigations enable to consider green ointment as harmless and safe for human health.

By bacteriological investigations it was stated that green ointment has bactericidal effect with the microbes of the following groups: Staphylococcus epidermidis, Streptococcus fecalis, Psevdomonas aeruginosa, Escherichia coli.

For the experiment was made the model of III degree burn on rabbits. The experimental group was treated with green ointment, the control group with 5% liniment of synthomycin.

By means of electric-paramagnetic resonance were examined the skin, liver, spleen, glands above kidneys and blood of experimental and control animals. In result of green ointment's effect the intensity of ribonucleotide-reductase, which indicates the growth of proliferation processes in spleen, was increased by 90% in comparison with control data. We can say that green ointment is an inductor of ribonucleotide-reductase.

Under the action of green ointment the intensity of nonhemic iron nitrizil complexes signal g=2.03, which testifies the reduction of after burn hypoxia degree in liver as well of methemoglobin and intensity of signals of $Mn^{2+}$ containing complexes, that is the indicative of hemolysis intensity and preservation of membrane structure enterity. It can be said that green ointment is characterized with membrane protective properties, which is determined by the reduction of lipides peroxide oxidation intensity. The indicative of membrane stabilizing effect is the reduction of oxidized ccruloplasmin signal and increase of $Fe^{3+}$ transferrin signal intensity in comparison with control data.

According to the results of the investigations carried out by means of electric-paramagnetic resonance method, green ointment reduces the intensity of lipides peroxide oxidation in cells, promotes for preservation of the enterity of membrane structure, reduces hypoxia degree in liver, effects proliferation processes and is an inductor of ribonucleotide-reductase.

The results of investigations show that under the effect of green ointment with experimental rabbits the primary-coat is removed earlier, than with the control animals, in result the healing process accelerated. The remove of the coat and healing acceleration makes 42.31% in comparison with 5% liniment of synthomycin. At the same time under the effect of green ointment the inflammatory processes in circulatory vessels is less expressed, microcirculation is not disrupted, thrombosis and stasis are not marked in the tissues around the wound. The widened capillaries refer to plasma capillaries, and that's why around the wound insignificant cell infiltration of blood elements is marked. These cell elements refer to the cells of tissue origin.

The comparison of healing rate and control rabbits shows, that healing acceleration in experimental animals is promoted by sharp activation of cell-tissue elements, increase of phagocytosis, increase of antioxidant activity of blood and tissues. The increase of phagocytosis and antioxidant activity of tissues causes the limitation of secondary alteration, the degradation of inflammatory process modulators and mediators activity, death of microorganisms.

It must be mentioned, that under the effect of green ointment the proliferation processes of connective tissues and epithelium elements are carried out simultaneously.

Under the effect of green ointment the immune cell circle is activated, the quantity of T lymphocytes is increased, the phagocytosis process is accelerated.

The application of present ointment enables:

widening of the assortment of medicinal preparations for burns and wounds;

increase of the treatment efficiency approximately for 42%.

The clinical approbation of green ointment was carried out in 6 clinics on 449 patients with different diagnosis. Among them, with infected and uninfected wounds —158 patients, with bum disease—75, with purulent damages of hypodermic tissues (carbuncle, furuncle, panaritium, abscess, phlegmon)—26, with trophic ulcers of different etiology—60, with cervical erosion and colpitis—130 patients.

The efficiency of green ointment action was evaluated by following criteria: general condition of a patient, visual evaluation of regeneration changes, epitalization terms of wound, ulcer and erosion surfaces, bacteriologic, cytological and colposcopy examinations.

The held examinations showed, that the application of green ointment at treatment of mentioned diseases causes the stimulation of regeneration processes, fast healing, the wounds are healed earlier than classic terms.

At treatment period there was observed the fast decrease of the purulent discharge, ache and edema of tissues around the wound, significant acceleration of wound clearing, improvement of microcirculation, the acceleration of peripheral epitalization processes.

At burn disease of I, II and III degrees with the patients there was observed the decrease and elimination of ache and plasmorrhea. The treatment results in complete epitalization without scars.

At treatment of acute colpitis the efficiency of ointment action was stipulated by its bactericidal action. After treatment in neither cases there was observed the increase of pathological microbes, the complete recovery of a patient takes place.

At cervical erosion the acceleration of epitalization processes, the recovery of mucous membrane takes place more faster than at treatment with other preparations.

At applying of green ointment there was no case of prolongation and complication of the disease.

On the basis of conducted investigations the green ointment is recommended by Pharmacological Committee as an effective medicinal means stimulating regeneration.

We claim:

1. An ointment for the treatment of burns and wounds in mammals, which comprises:

| | |
|---|---|
| Chelidonium majus | 15–25 g; |
| Plantago major | 15–25 g; |
| Matricaria chamomilla | 15–25 g; |
| Achillea millefolium | 15–25 g; |
| Calendula officinalis | 15–25 g; |
| Hypericum perforatum | 15–25 g; |
| Eucalyptus globulus | 15–25 g; |
| Oleum olivarum | 1000 g; and |
| Cera flava | 80–130 g. |

2. A method for the treatment of burns and wounds in mammals, which comprises:

applying to the site of a burn or a wound a burn-healing or a wound-healing effective amount of an ointment comprising

*Chelidonium majus* 15–25 g;

*Plantago major* 15–25 g;

*Matricaria chamomilla* 15–25 g;

*Achillea millefolium* 15–25 g;

*Calendula officinalis* 15–25 g;

*Hypericum perforatum* 15–25 g;

*Eucalyptus globulus* 15–25 g;

*Oleum olivarum* 1000 g and

*Cera flava* 80–130 g.

* * * * *

UNITED STATES PATENT AND TRADEMARK OFFICE
CERTIFICATE OF CORRECTION

PATENT NO. : 5,997,876
DATED : December 7, 1999
INVENTOR(S) : SHIKHASHVILI ET AL.

It is certified that error appears in the above-identified patent and that said Letters Patent is hereby corrected as shown below:

On the Title Page

[76] Delete "Ga." both occurrences, insert -- GE.--
Delete "38012", insert -- 380012 --.

[30] Foreign Application Priority Data
Delete "[GA]", insert -- [GE.] --.

In the Specification

Column 3, lines 8 and 13 and Column 4, line 9, delete "III", insert --III$^b$--, In the Claims Column 5, line 9, delete "bum", insert --burn--.

Signed and Sealed this

Tenth Day of April, 2001

Attest:

NICHOLAS P. GODICI

Attesting Officer — Acting Director of the United States Patent and Trademark Office